United States Patent [19]
Ayers et al.

[11] Patent Number: 5,266,731
[45] Date of Patent: Nov. 30, 1993

[54] ELECTROCATALYTIC HYDROGENATIONS OF NITRILES TO AMINES

[75] Inventors: William M. Ayers, Princeton; Mary H. Dean, Elizabeth, both of N.J.

[73] Assignee: Reilly Industries, Indianapolis, Ind.

[21] Appl. No.: 731,807

[22] Filed: Jul. 17, 1991

[51] Int. Cl.$^5$ .............................. C07C 209/48
[52] U.S. Cl. .................. 564/492; 204/73 A; 564/415; 564/448; 564/490; 564/491; 564/493
[58] Field of Search .................. 564/492, 415; 204/157.81, 73 R, 181.4, 74, 73 A

[56] References Cited

U.S. PATENT DOCUMENTS 3,925,173 12/1975 Junghans .................. 204/73 R
4,584,069 11/1986 Lessard et al. .................. 204/74
5,066,374 11/1991 Winkle .................. 204/181.4

OTHER PUBLICATIONS

Semiconducting and Electrocatalytic Properties of Sputtered Cobalt Oxide Films, Schumacher, L. C. and Holzhueter, I. B. Translated from Elektrokhimiya, vol. 35, No. 6 pp. 975–984 (1990).

Electrocatalytic Reduction of Adiponitrile—A. P. Tomilov, I. V. Kirilyus, and I. P. Andriyanova (1972) Consulants Bureau Translated from Elektrokhimiya, vol. 8, No. 7, pp. 1050–1052 Jul. 1972.

*Primary Examiner*—Glennon H. Hollrah
*Assistant Examiner*—Brian M. Burn
*Attorney, Agent, or Firm*—Woodard, Emhardt, Naughton, Moriarty & McNett

[57] ABSTRACT

Described are processes for producing amines from nitriles. The processes include electrocatalytic hydrogenations of nitriles in the presence of transition metal-oxide and/or transition metal-hydroxide cathodes to thereby form amines. Preferred modes of the invention provide highly advantageous processes for producing hexamethylenediamine from adiponitrile.

29 Claims, No Drawings

ELECTROCATALYTIC HYDROGENATIONS OF NITRILES TO AMINES

BACKGROUND OF THE INVENTION

The present invention relates generally to electrocatalysis, and more particularly to unique metal-oxide electrocatalysts and their use in reduction processes for producing amines from nitriles.

Hydrogenation of nitriles to amines has long enjoyed substantial academic and commercial interest. It is recognized that these hydrogenations require a catalyst to promote reduction for best efficiency. On all scales, and particularly on a commercial scale, most such reductions are conducted by simply passing chemical reactants of choice, usually substrate plus hydrogen, over catalysts at elevated temperatures and pressures. This has generally been termed a "secular" type reaction. For example, Raney nickel is one of the most widely used catalysts for secular hydrogenations to produce amines from nitriles. As is well known, Raney nickel is a high surface area material derived by leaching the aluminum from a nickel/aluminum alloy. The resulting nickel material, in spite of its recognized pyrophoric nature, has become a hydrogenation catalyst of choice.

For example, much work has focussed upon Raney nickel catalyzed hydrogenations of adiponitrile (ADN) to hexamethylenediamine (HMD). HMD is a large volume, highly useful chemical, notably in large amounts as a Nylon 6,6 intermediate. The secular catalytic hydrogenations used today in large scale HMD production require high pressures, high temperatures, and an expensive (usually Raney Ni) catalyst. Moreover, these secular hydrogenations have been known to form undesirable by-products removable only with great difficulty and expense, if at all. Often, these by-products significantly interfere with the use of the formed amine. For instance, Raney Ni catalyzed reduction of ADN to HMD is known to form 1,2-diaminocyclohexane (DAC), which is not readily separated from the HMD product. This DAC by-product is then included in the HMD during processing to form Nylon, which, as those in industry know, leads to highly undesirable discoloration of the Nylon. Nonetheless, as already stated, much work still focuses on such secular catalytic processes, with more recent work emphasizing process refinements. See, U.S. Pat. Nos. 3,821,305; 4,247,481; and 4,359,585. In addition to the nickel catalysts, Raney cobalt borohydride has been reported as a heterogeneous catalyst for secular catalytic hydrogenations of ADN to HMD. See, Japanese patent No. 7511138 (1979).

Despite many potential advantages to be gained, the study of electrocatalytic (i.e. cathodically catalyzed) approaches to hydrogenating nitriles has generally failed to keep pace with that of secular-type reactions. There are relatively few such electrocatalytic studies reported, most originating from the U.S.S.R. As an example, early on, A. P. Tomilov developed and reported an electrochemical process for direct reduction of ADN to HMD. Tomilov, A.P., "Electrochemical Synthesis of Hexamethylenediamine and Aminocaponitrile", Khim. Prom. 329-333 (1965); see also Soviet Patents 137,924 (1961) and 445,647 (1974) (cited in Kuhn, A. T., "Industrial Electrochemical Processes", Elsevier Pubs., New York, pp. 609-610 (1971)). This original process utilized copper sponge-covered steel metal cathodes and magnetite anodes. A sodium hydroxide electrolyte was used at a 20-50 cm/sec electrolyte velocity, which was needed to maintain ADN as an emulsion. Current density was 60 mA/cm2. Under these conditions, a total current efficiency of 51% was reportedly obtained, with the product ratio being 4.4:5.6, HMD:Aminocaponitrile, or 44% HMD.

In later work, Tomilov changed the process to include a diaphragm and paired production of chlorine at the anode. Accordingly, in this newer work the anolyte was 25-30% HCL, and the catholyte 96.9 g/L ADN in NaOH. Further, a nickel metal sponge cathode was used, as was a current density of 100 mA/cm$^2$. Under these conditions, the reported total yield improved from 51% to 72%, with the yielded product being 60% HMD and 12% aminocaponitrile (ACN). It was not reported why better yields obtained in the later work. However, it was claimed that the process could produce HMD at 20% lower cost than secular-type catalytic hydrogenation. Rounding out this work in the U.S.S.R. is a "Deposited Document" which relates to optimization of an electrocatalytic process for reducing ADN, this time using a Raney iron electrocatalyst. Andriyanaova, I. P. et al., "Optimization of Electrocatalytic Reduction of Adiponitrile on Raney Iron", Deposited Doc. Khim. Metal Inst., Karaganda USSR (1980).

Despite this work in the U.S.S.R. and Tomilov's claim of low cost HMD production, to applicant's knowledge, no electrocatalytic route to HMD as been adopted commercially. This may be because the secular catalytic hydrogenation processes have been highly optimized, and any displacement of them commercially will have to come from an electrocatalytic process achieving markedly high efficiency. Such an electrocatalytic process would offer significant advantage over secular processes in providing low cost routes to HMD and other amines, but, up to now, no such process appears to have demonstrated the requisite efficacy. The applicant entered a study in light of this background, and has now discovered unique cathodic electrocatalysts which provide preferred processes of surprisingly high efficiency.

SUMMARY OF THE INVENTION

Accordingly, one preferred embodiment of this invention relates to a process for producing an amine from a nitrile. The process includes the step of electrocatalytically hydrogenating the nitrile in the presence of a cathode including an effective catalytic amount of transition metal-oxide or transition metal-hydroxide or a mixture thereof. In contrast to previously known work which suggests that metals themselves should be used as cathodic electrocatalysts, the applicant has discovered that these metal-oxide and/or metal-hydroxide cathodes surprisingly catalyze hydrogenations. Cathodes containing one or more oxides and/or hydroxides of cobalt or of iron are preferred, and particularly preferred processes involve electrocatalytic production of hexamethylenediamine from adiponitrile. These preferred processes provide important electrocatalytic routes which achieve high yields of product having fewer impurities than Raney-nickel based and other secular hydrogenation routes, as well as additional objects and advantages which will be apparent from reviewing the following description and appended claims.

DESCRIPTION OF THE PREFERRED EMBODIMENT

For the purposes of promoting an understanding of the principles of the invention, reference will now be made to certain embodiments and specific language will be used to describe the same. It will nevertheless be understood that no limitation of the scope of the invention is thereby intended, such alterations, further modifications and applications of the principles of the invention being contemplated as would normally occur to one skilled in the art to which the invention relates.

As stated above, one preferred embodiment of the invention relates to electrocatalytic hydrogenations (i.e. reductions) of amines to nitriles, conducted in the presence of a cathode catalyst of a transition metal-oxide or transition metal-hydroxide or a mixture thereof. In this regard, as is well known, electrocatalysis refers to catalytic effect resulting from enhanced rate of electron transfer by an electrode to or from a substrate, as well as to all reactions following, preceding, or concurring with the electron transfer. The preferred electrocatalytic reactions of this invention can be carried out in any suitable electrochemical cell arrangement. These include, for example, flow or static cells, operable in batch or continuous modes, packed bed and parallel plate cell configurations, etc.

The metal-oxide and/or metal-hydroxide cathode can be formed from any suitable transition metal. Transition metal oxides or hydroxides can be those which, prior to this invention, had been conventionally used as anodic electrocatalysts. These include, for example, oxides and/or hydroxides of group IB, IIB, and IIIA-VIIIA elements (CAS version), with more preferred being group VIII or VIIIA metal oxides and/or hydroxides, and most preferably oxides and/or hydroxides of cobalt or iron based on work to date. These effective cathodes can contain an oxide or hydroxide of the selected metal or mixtures of various oxides and/or hydroxides of the metal or mixtures with other metals, metal oxides and/or hydroxides, or nonmetals.

The physical attributes of the cathode have not proven critical thus far. Accordingly, the cathode may be formed from foils, expanded mesh, wires, beads, discs, powders, etc, with foil and bead form metals being preferred from work to date. Additionally, oxides or hydroxides can be formed on metal alloys, for instance cobalt alloys, as well as doped or supported metal materials, which are also acceptable for the invention.

The preferred effective, substantial oxide and/or hydroxide stratum is characterized by its thickness significantly greater than those resulting from adventitious oxidation of cobalt metal in air at temperatures below 200° C., or in situ under normal cell operating conditions. In applicant's work, thick, effective films have been formable by either annealing the cobalt, iron or other metal, preferably in air in the presence of water vapor, or by chemical means. With cobalt, this can be achieved, for example, by heating the cobalt in a water-containing atmosphere at a temperature greater than 200° C. but less than about 900° C. for about 20 minutes to many hours, preferably about 500° C. Highly successful annealing procedures have also been conducted by annealing the cobalt or other metal for 20 minutes at 500° C., followed by applying water to the annealed material and annealing again at 500° C./20 min. These annealing procedures provide effective films containing oxides and/or hydroxides, e.g. in the case of cobalt, $Co_3O_4$ (i.e. cobaltic-cobaltous oxide) and/or hydrates thereof, and/or $Co(OH)_2$ (i.e. cobaltous hydroxide). Chemical oxidation of metals to form substantial oxide coatings has worked well also. For instance, treatment of steel plates or other structures with baths known to produce red, blue, or black oxide coatings can produce effective cathodes. For steel, these are usually basic pH baths containing nitrates, nitrites, and/or chromates.

Applying metal-oxide and/or hydroxide to conductive substrates will also be suitable for the invention. These catalysts may conveniently be in powder form with or without binders or adhesive agents. For instance, powders containing oxides of the selected metal, for example cobalt oxides or mixtures thereof, can be used to coat conductive substrates such as nickel screens or steel discs or plates. Such effective cobalt oxide catalysts to date have included, for example, $Co_3O_4$, as well as hydrates thereof. Non-powder metal-oxide forms such as prilled spheres or granules are also acceptable, and are accordingly contemplated as being within the scope of the invention. Other procedures by which effective, substantial transition metal-oxide and/or hydroxide films can be made achieving the same significant results consistent with the Examples below are, of course, also contemplated as being within the scope of the invention. The electrocatalytic materials thus formed can be used immediately to high advantage, but also can be effectively stored, preferably under deionized water, for later use.

Conventional anodes can be used in the inventive processes. These can include, for instance, metal foils or beads, as well as Dimensionally Stable Anodes (DSA's) such as platinized DSA's. As those skilled in the field will understand, however, many other materials of varying physical configuration are suitable anodes and can be used. Preferred anode materials are those having low oxygen overvoltages, as well as being relatively inert to the nitrile reactants and amine products (e.g. ADN, AMCN and HMD) in the event these reactants and products are subjected to potentially adverse anodic reactions. In this regard, in the preferred cell configurations, the anode and cathode compartments are separated so that the anolyte remains at least substantially free from reactants and/or products which may potentially pass from the catholyte during the reaction. To date, CELGARD available from Celanese Corporation and NAFION separators available from Du Pont, have proven suitable for this purpose, although many other separators are known and can be used in the inventive processes.

The preferred reactions are also conducted in the presence of auxiliary salts. For instance, as to cations, potassium, lithium and sodium salts have proven suitable, with potassium and sodium salts being more preferred among these three. As to anions, phosphate, sulfate, hydroxide, carbonate and fluoride salts are acceptable, with phosphate and floride salts being more preferred. Accordingly, more preferred salts are those such as potassium phosphate, sulfate and fluoride, as well as sodium and lithium phosphate, with potassium phosphate being most preferred thus far. Additionally, preferred reactions can be conducted in the presence of suitable buffer systems, for instance phosphate buffer, to stabilize the pH of the reaction medium. As will be understood, however, many other suitable auxiliary salts and buffers are known and can be used within the scope of the invention.

Likewise, other parameters such as temperature, use of co-solvents, current densities, potential applied, and total charge passed will vary with the particular chemistries involved and are well within the manipulative skills of those practiced in this field.

The reactants of the invention are conventional. They include a wide variety of nitriles known for their susceptibility to catalytic hydrogenation to amines. For example, reference can be made to R. L. Augustine, "Catalytic Hydrogenation", Marcel Debber, New York, 1965; Paul N. Rylander, "Catalytic Hydrogenation over Platinum Metals", Academic Press, New York, 1967, which provide a good discussion of nitrile hydrogenations to amines. In this regard, one preferred mode of carrying out the invention involves electrocatalytic hydrogenation of ADN to HMD and AMCN and further reduction of AMCN to HMD using cobalt oxide and/or hydroxide electrocatalysts. This hydrogenation has proven particularly advantageous, and leads to very efficient production of HMD with current efficiencies ranging above 60% and even up to 80% and more. Additionally, in accordance with the invention HMD has been produced in high selectivity over AMCN, for instance, greater than about 5 to 1 (mole to mole), and even ranging to and above about 10 to 1, as illustrated in the specific Examples below.

Further, in the applicant's work, the product has been free from any detectable amount of 1,2-diaminocyclohexane (DAC). This is an important aspect, since DAC, a well-known byproduct of many current secular catalytic hydrogenations of ADN to HMD, is known to cause darkening and discoloration of final products. This has been and remains a substantial concern in the nylon industry, the primary consumer of all HMD produced in the world. The invention thus directly addresses this concern, while further providing many additional significant advantages as discussed above.

While the invention has been illustrated and described in detail in the foregoing description, the same is to be considered as illustrative and not restrictive in character, it being understood that only certain preferred embodiments have been described and that all changes and modifications that come within the spirit of the invention are desired to be protected.

All publications cited or referred to in this application are hereby incorporated by reference as if set forth fully herein.

For the purposes of promoting a better understanding of the principles and advantages of the present invention, the following Examples are provided.

EXAMPLE 1

Preparation of Parallel Plate Reactor

A parallel plate reactor was Prepared having a platinum anode and a cobalt-based cathode mounted on opposite endplates. The cathode consisted of 6 $cm^2$ Cobalt foil which had been annealed in the presence of water vapor at a temperature of 500° C. for a period of 20 minutes. This treatment formed a layer of substantial thickness on the foil containing oxides and hydroxides of cobalt. The anode was platinum foil. A 3.1 mm thick rigid Teflon spacer was placed over each endplate, and a CELGARD separator available from Celanese Corporation, was pressed between the spacers. A MASTERFLEX peristaltic pump drive with two heads continuously recycled the anolyte (100 ml) and catholyte (30 ml) at a rate of 80 ml per minute. C-FLEX flexible tubing (available from Cole-Parmer, Inc. of Chicago, Ill.), which is inert toward nitriles and amines, was used throughout the system. The potential of the cathode was measured with respect to a Ag/AgCl reference electrode inserted through the reactor endplate and positioned below the cathode. Potential and cell voltage were recorded with a BAS CV-27 potentiostat operating in the electrometer mode and a Heath Model SR-206 dual pen chart recorder. Current was supplied by an HP Model 6216B DC power supply, and the current and cell voltage were measured with miltimeters.

EXAMPLES 2-6

Comparison of Cathode Materials

The importance of the film formed on the cathode such as formable by the annealing procedure of Example 1 was demonstrated in a series of experiments in which the performance of a cell as described in Example 1 was compared to that of similar cells but having cobalt cathodes treated as indicated in Table 1. Respective catholytes (30 ml) and anolytes (100 ml) were prepared having 0.1 M adiponitrile (ADN) and 0.5M $K_3PO_4$. A 75 mA/$cm^2$ constant current was applied for one hour, after which the catholyte was analyzed for organics using gas chromatography. The results of this testing are set forth in Table 1. While the reported figures reflect some experimental error (estimated particularly in Examples 5 and 6 to be about ±6%), they nevertheless demonstrate the dramatic improvement in hexamethylenediamine (HMD) production rate and efficiency which occurs when cathodes having a substantial oxide and/or hydroxide stratum or content are used. Additionally, the electrolyzed catholyte contained no detectable 1,2-diaminocyclohexane (DAC), which is highly important since the significant presence of DAC. in HMD during common industrial processing can lead to substantial and undesirable discoloration of final products.

TABLE 1

| Ex. | Cathode Treatment | Current Efficiency (%)[a] | | |
|---|---|---|---|---|
| | | AMCN | HMD | TOTAL |
| 2 | Abrasive only | 10.0 | 7.1 | 17.1 |
| 3 | $NH_4OH$ washed | 2.8 | — | 2.8 |
| 4 | Anodic Film | 10.4 | — | 10.4 |
| 5 | Annealed Film | 3.8 | 97.6 | 101.4 |
| 6 | Annealed Film | 2.0 | 104.4 | 106.4 |

[a]% Current Efficiency = (n * F * Rate of Formation)/Current Density * 100, where n = 4 for AMCN and n = 8 for HMD.

EXAMPLES 7-10

Hydrogenations With Varying Electrolytes

In another series of experiments, various electrolytes were tested in inventive processes. Accordingly, respective catholytes (30 ml) and anolytes (100 ml) were prepared having 0.1M ADN and the electrolytes indicated in Table 2 in a concentration of 0.5M. These electrolytes were then reacted in the parallel plate reactor as described in Example 1. A constant current of 75 mA/$cm^2$ was applied during the reaction, which was allowed to proceed for 1 hour. The results shown in Table 2 again in some instances reflect experimental error, but likewise convincingly demonstrate further preferred processes achieving successful and selective production of HMD from ADN in accordance with the invention.

TABLE 2

| Ex. | Electrolyte | Current Efficiency (%)[a] | | |
|---|---|---|---|---|
| | | AMCN | HMD | TOTAL |
| 7 | KF | 3.1 | 74.5 | 77.6 |
| 8 | $K_3PO_4$ | 3.8 | 97.6 | 101.4 |
| 9 | $K_3PO_4$ | 2.0 | 104.0 | 106.4 |
| 10 | $(NH_4)_2HPO_4$ | 8.8 | 29.1 | 37.9 |

[a] Current Efficiency = (n * F * Rate of Formation)/Current Density * 100, where n = 4 for AMCN and n = 8 for HMD.

EXAMPLES 11–16

Packed Bed Cell Hydrogenations

For Examples 11–13, a packed bed-parallel plate cell was constructed by modifying a parallel plate reactor in the following ways. In the cathode compartment, 15 cm² of cadmium foil was attached to the endplate. Contact was made to the cadmium foil by a 1 mm diameter palladium wire through the back of the cell so as to prevent contact between the palladium and electrolyte. The cathode compartment was packed with 40 cm² of cobalt beads, annealed similarly to the cobalt foil in Example 1 (500° for 20 minutes). The beads were held in place by plastic screens placed over the electrolyte inlet and outlet, and a fine mesh plastic screen separated the beads from the CELGARD separator. The anolyte and catholyte were circulated separately each at a 80 ml/min. using a MASTERFLEX pump drive with two heads. The current source was an HP 6284A DC power supply. A total current of 3 A was used, for which the average current density was about 75 mA/cm². The supporting electrolyte was 0.5M $K_3PO_4$, and the initial ADN concentration was 0.2M. The electrolyses reported (Examples 1, 12 and 13) were each 20 minutes in duration and were run run successively in the cell, reusing the beads each time without intervening treatment. The results, reported in Table 3, surprisingly demonstrate increasing rates and current efficiencies with each subsequent use of the beads, reaching a high current efficiency of 90% in Example 13.

For Examples 14–16, a packed cell as described above was used, except instead of platinum foil, two layers of extended mesh platinized DSA were mounted on the endplate opposite the beads to provide an anode. As such, the DSA was in direct contact with the CELGARD, thus reducing the cell gap and decreasing the cell voltage. The anolyte and catholyte were circulated separately at a flowrate of 142 ml/min. Again, a total current of 3 A was used, for which the average current density was about 75 mA/cm². As before, the supporting electrolyte was 0.5M $K_3PO_4$, and the ADN concentration 0.2M. The electrolyses were again run successively, each lasting was 16 minutes. The resulting rates of formation and current efficiencies are set forth in Table 4.

TABLE 3

| Example | Anode | HMD Current Efficiency (%) |
|---|---|---|
| 11 | Pt foil | 48 |
| 12 | Pt foil | 68 |
| 13 | Pt foil | 90 |

TABLE 4

| Example | Anode | Current Efficiency (%) | | |
|---|---|---|---|---|
| | | HMD | AMCN | TOTAL |
| 14 | Platinized DSA | 65.2 | 5.4 | 70.6 |

TABLE 4-continued

| Example | Anode | Current Efficiency (%) | | |
|---|---|---|---|---|
| | | HMD | AMCN | TOTAL |
| 15 | Platinized DSA | 58.4 | 6.6 | 65.0 |
| 16 | Platinized DSA | 67.3 | 6.6 | 73.9 |

EXAMPLES 17–19

Electrocatalyses Using Various Cathodes

A series of runs were conducted to test the ability of other transition metal-oxide/metal-hydroxide cathodes to electrocatalyze hydrogenation of nitriles to amines. Accordingly, in these runs an electrochemical cell as described in Example 1 above was used, except employing as cathodes respective foils of zinc, iron and nickel instead of the cobalt foil. The Zn, Fe and Ni foils were annealed in the presence of water vapor similarly to the Co foils in the preceding Examples. Again, the anolytes used (100ml) contained 0.5M $K_3PO_4$, and the catholytes (30 ml) contained 0.1M ADN and 0.5M $K_3PO_4$. A constant current of 75 mA/cm² was applied during these experiments, and the electrolysis time was 60 minutes for each run. The results, summarized in Table 5, demonstrate the capacity of the transition metal-oxide/metal-hydroxide cathodes to act as effective electrocatalysts for hydrogenation of nitriles to amines. This is in marked contrast to the art-recognized teaching that reduced metals should be used as reductive electrocatalysts. In Table 5, "—" indicates that no amount of the relevant product was detected.

TABLE 5

| Example | Cathode | Current Efficiency (%) | |
|---|---|---|---|
| | | HMD | AMCN |
| 17 | Nickel | 5.0 | — |
| 18 | Iron | 37.1 | 5.1 |
| 19 | Zinc | 3.4 | — |

EXAMPLES 20–21

Electrocatalytic Hydrogenations With $Co_3O_4$ Cathodes

Two $Co_3O_4$ cathodes were prepared. One cathode was prepared by pressing $Co_3O_4$ powder onto the surface of four 7.7 mm diameter steel disks (for a total cathode surface area of 1.9 cm²). These disks were soldered to copper wire contacts, and all surfaces except the $Co_3O_4$ were covered with epoxy. Another cathode was prepared by pressing $Co_3O_4$ powder onto a 250 mesh nickel screen. The screen was visually examined against an illuminated background, which indicated that it was completely covered with the powder. The surface area of this cathode was 6.3 cm².

Each of these cathodes was then mounted and used in a cell such as that described in Example 1 to electrocatalytically hydrogenate ADN to HMD. In each of these experiments, the anolytes (100 ml) were 0.5M $K_3PO_4$, and the catholytes (30 ml) were 0.1M ADN and 0.5M $K_3PO_4$. A constant potential of −1.5 V was used in each experiment for a duration of two hours, with current efficiency being measured each hour. The results are set forth in Table 6 below. They demonstrate the efficacy of $Co_3O_4$ cathodes in reductive electrocatalysis of nitriles to amines. Further, no AMCN was detected in either experiment, illustrating the very high selectivity of these cathodes for HMD over AMCN.

TABLE 6

| Example | Cathode | Hr. 1 Current Efficiency (%) | | Hr. 2 Current Efficiency (%) | |
|---|---|---|---|---|---|
| | | HMD | AMCN | HMC | AMCN |
| 20 | Co$_3$O$_4$/disks | 47.0 | — | 46.0 | — |
| 21 | Co$_3$O$_4$/mesh | 53.0 | — | 67.0 | — |

EXAMPLES 22-26

Packed Bed Cell Hydrogenations With Cobalt Oxide Coated Beads

Several packed bed cell hydrogenations were conducted similar to those in Examples 11-16. This time, however, the cathodes included cobalt oxide films formed on underlying substrates. Both electrodeposition or electroless deposition of cobalt were used in the preparation of the films.

Accordingly, cobalt oxide (e.g. Co$_3$O$_4$) cathodes were prepared by electrodeposition of cobalt on various kinds of solid shot, followed by annealing the cobalt deposit (as in Example 1) to form the oxide. The shots used were made, respectively, of carbon steel (Example 22), zinc plated steel (Example 23), and chrome steel (Example 24).

An additional cathode (Example 25) was prepared by electroless deposition as follows: 160 steel beads of 4.5 mm diameter were cleaned in acetone and rinsed with deionized water. An electroless cobalt plating bath consisting of cobalt chloride, sodium citrate, ammonium chloride and sodium hypophosphate reducing agent [Electroplating Engineering Handbook, L. J. Dunnay (ed. pp. 439-440, Van Nostrand Reinhold Press] was added to a rotating flask containing the beads. The PH of the solution was adjusted to 9.5 with ammonium hydroxide. The temperature of the flask was brought to 90°-95° C. and the beads were coated during a two hour exposure to the plating solution. After two hours, the solution was drained from the flask and a fresh plating solution was added to the flask. The beads were coated for another two hours, drained of solution and rinsed. The beads gained 2.36 miligrams each of cobalt from the plating process. The beads were then annealed at 500° C. for 20 minutes in the presence of water vapor, quenched in deionized water until their temperature reached 60° C., then annealed again at 500° C. for an additional 20 minutes in the presence of water vapor.

Each of these cathode materials was individually used to electrocatalytically hydrogenate ADN to HMD in a packed bed electrochemical cell. More specifically, 0.1M ADN was used in each case, and the cells were operated at a cathode potential of approximately −2.3 V vs. Ag/AgCl. In these experiments HMD current efficiencies of about 64% and AMCN current efficiencies of about 3% were obtained during the first hour of operation.

Still another cathode (Example 26) was prepared by the above-described electroless deposition procedure, except replacing the sodium hypophosphate reducing agent with methyl borane reducing agent. Use of this cathode in a packed bed electrochemical cell with 0.1M ADN and a cathode potential of approximately −2.3 V vs. Ag/AgCl provided current efficiencies for HMD and AMCN of about 67% and 4%, respectively, during the first hour.

What is claimed is:

1. A process for producing an aliphatic or aromatic amine from a corresponding aliphatic or aromatic nitrile, comprising the step of electrocatalytically hydrogenating the nitrile in the presence of a cathode including an effective catalytic amount of a cobalt metal-oxide or a mixture thereof with a cobalt metal-hydroxide.

2. A process according to claim 1, wherein said cathode includes a coating having an effective catalytic amount of metal oxide and/or metal-hydroxide on an underlying metal.

3. A process according to claim 1, wherein said cathode is formable by annealing cobalt metal.

4. A process according to claim 3, wherein said annealing is conducted in the presence of water vapor.

5. A process according to claim 1, wherein said cathode contains an effective catalytic amount of Co$_3$O$_4$.

6. A process according to claim 1, wherein said cathode contains an effective catalytic amount of Co(OH)$_2$.

7. A process according to claim 1, wherein the nitrile is adiponitrile and the amine is hexamethylenediamine.

8. A process according to claim 1, conducted in an electrochemical cell having separated anode and cathode compartments whereby the amine and nitrile at least substantially remain in the cathode compartment.

9. A process according to claim 8, wherein said amine is produced at a current efficiency of at least about 60%.

10. A process according to claim 9, and also including the step of isolating said amine.

11. A process according to claim 10, in which the cell has an anode having a low oxygen overvoltage.

12. A process according to claim 11, conducted in the presence of a sodium or potassium salt.

13. A process according to claim 11, conducted in the presence of a hydroxide, carbonate, fluoride or phosphate salt.

14. A process according to claim 12, wherein said salt is sodium phosphate or potassium phosphate.

15. A process according to claim 10, wherein said cathode is formable by annealing cobalt metal.

16. A process according to claim 15, wherein said annealing is conducted in the presence of water vapor.

17. A process according to claim 16, wherein said cobalt which is annealed is in foil, expanded mesh, screen, wire or bead form.

18. A process according to claim 17, wherein said cobalt which is annealed is in bead form, and wherein said cathode includes a packed bed of the resulting annealed beads.

19. A process according to claim 18, wherein said cell is a parallel plate reactor.

20. A process according to claim 17, wherein said cobalt which is annealed is in foil form, and wherein said cell is a parallel plate reactor.

21. A process according to claim 17, wherein the nitrile is adiponitrile and the amine is hexamethylenediamine.

22. A process according to claim 21, wherein the hexamethylenediamine is produced at a selectivity of at least about 5 to 1 with respect to any aminocaponitrile produced.

23. A process according to claim 22, wherein the hexamethylenediamine is produced at a selectivity of at least about 10 to 1 with respect to any aminocaponitrile produced.

24. A process according to claim 22, where the hexamethylenediamine is produced essentially free from any 1,2-diaminocyclohexane.

25. A process according to claim 23, wherein the hexamethylene diamine is produced at a current efficiency of at least about 80%.

26. A process for producing an aliphatic or aromatic amine from a corresponding aliphatic or aromatic nitrile, comprising the step of electrocatalytically hydrogenating the nitrile in the presence of a cathode formable by annealing cobalt metal.

27. A process according to claim 26, wherein the nitrile is adiponitrile and the amine is hexamethylene diamine.

28. A process according to claim 26, wherein the annealing is in the presence of water vapor.

29. A process according to claim 27, wherein the cathode comprises an effective catalytic amount of $Co_3O_4$.

* * * * *